United States Patent [19]

Nishio et al.

[11] Patent Number: 4,668,477
[45] Date of Patent: May 26, 1987

[54] GAS SENSOR

[75] Inventors: Hisaharu Nishio, Tokai; Kazuo Taguchi, Nagoya; Toshio Okumura, Kakamigahara; Akio Ebizawa, Iwakura, all of Japan

[73] Assignee: NGK Spark Plug Co., Ltd., Nagoya, Japan

[21] Appl. No.: 631,204

[22] Filed: Jul. 16, 1984

[30] Foreign Application Priority Data

Jul. 21, 1983 [JP] Japan ............... 58-113578[U]

[51] Int. Cl.⁴ .................................... G01N 27/46
[52] U.S. Cl. .................................. 422/98; 204/428; 73/23
[58] Field of Search ................ 73/23, 27 R; 204/424–429; 338/34; 340/632–634; 422/94–98; 436/127, 137

[56] References Cited

U.S. PATENT DOCUMENTS

| | | | |
|---|---|---|---|
| 2,686,081 | 8/1954 | Cooksley | 222/511 |
| 4,111,778 | 9/1978 | Davis et al. | 204/428 |
| 4,187,163 | 2/1980 | Steinke et al. | 73/23 X |
| 4,210,510 | 7/1980 | Grimes | 204/428 |
| 4,219,399 | 8/1980 | Gruner et al. | 204/428 X |
| 4,264,424 | 4/1981 | Niedrach | 204/421 |
| 4,320,378 | 3/1982 | Taniguchi et al. | 73/27 R X |

FOREIGN PATENT DOCUMENTS

| | | | |
|---|---|---|---|
| 2738882 | 3/1978 | Fed. Rep. of Germany | 204/429 |
| 57-103045 | 6/1982 | Japan | 204/424 |

OTHER PUBLICATIONS

Halliwell, Heat Resistant Resin for Industrial Uses, Modern Plastics, Nov. 1947.

*Primary Examiner*—Barry S. Richman
*Assistant Examiner*—Michael S. Gzybowski
*Attorney, Agent, or Firm*—Oblon, Fisher, Spivak, McClelland & Maier

[57] ABSTRACT

A gas sensor including a gas sensor body in which is centrally inserted a gas detecting element and which permits the gas sensor itself to be attached to other members; a protective sleeve attached to an end portion of the gas sensor body; a seal member formed of a heat-resistant synthetic resin, the seal member being disposed inside an end portion on a lead wire draw-out side of the protective sleeve, with a lead wire extending through the seal member; and a spring member mounted within the protective sleeve for urging the seal member liquid-tightly against the lead wire draw-out side end portion of the protective sleeve. Since the seal member disposed in an end portion of the protective sleeve is formed of a heat-resistant synthetic resin, the durability thereof is improved even where high temperature gases such as the exhaust gases of internal combustion engines or the like are to be detected. Moreover, since the seal member is pushed against the end portion of the protective sleeve, no gas is formed between the protective sleeve and the seal member, whereby the ingress of liquid can be prevented.

10 Claims, 4 Drawing Figures

GAS SENSOR

BACKGROUND OF THE INVENTION

1. Field of the Invention

The present invention relates to a gas sensor superior in both liquid ingress preventing property and durability. More particularly, it is concerned with a gas sensor having a gas detecting element and a structure which permits the gas sensor itself to be attached to other members and is capable of preventing the ingress of liquid to the gas detecting sensor and improving durability.

2. Discussion of the Background

Heretofore there has been known a concentration cell type gas sensor for detecting a certain kind of gas component contained in the exhaust gases of internal combustion engines or various combustion apparatus. For example, an oxygen sensor for detecting oxygen contained in the exhaust gases of an automobile engines is of a structure which permits the introduction of air (oxygen) into the reference electrode-side interior of an oxygen detecting element. However, in the event of entry of a liquid such as water or oil into the interior of the detecting element, the liquid is vaporized by the heat of the exhaust gases and produces a gas or gases other than oxygen with the result that a required electromotive force is not obtained and it therefore becomes impossible to exactly detect oxygen in the exhaust gases. In an effort to eliminate such an inconvenience, prior art devices utilize a structure as shown in FIG. 1, in which a seal member 6 made of rubber is attached through a spacer 8 to an end portion of a sensor protecting sleeve 4 which is mounted to a metallic body 2, so as to prevent the ingress of liquid such as water or oil into an oxygen detecting element (zirconia element) 10. But, since the exhaust gases from automobiles have fairly high temperatures (about 700°-800° C.), such rubber seal member cannot afford sufficient heat resistance and its life is short.

On the other hand, by using a seal member formed of a heat-resistant synthetic resin, it is possible to improve the heat resistance and prolong the life of such seal member but a satisfactory seal cannot be ensured because of its poor elasticity.

SUMMARY OF THE INVENTION

The present invention has been accomplished in view of the above-mentioned circumstances, and it is an object thereof to provide a gas sensor for detecting a gas component contained in the exhaust gases of internal combustion engines or various combustion devices, for example, a gas sensor for detecting an oxygen component contained in the exhaust gases from an automobile engine.

It is another object of the present invention to provide a gas sensor capable of improving both the liquid ingress preventing property of a seal member for preventing the ingress of liquid such as water or oil and to provide durability against heat.

It is a further object of the present invention to provide a gas sensor with little leakage of air from a seal member.

It is a still further object of the present invention to provide a gas sensor which permits easy welding between a metallic body and a protective sleeve.

The gist of the present invention which has been effected for achieving the above-mentioned objects resides in that in a gas sensor having a body in which is centrally inserted a gas detecting element and which permits the gas sensor itself to be attached to other members, and a protective sleeve attached to an end portion of the body, a seal member formed of a heat-resistant synthetic resin with a lead wire passing therethrough is disposed inside an end portion on the lead wire draw-out side of the protective sleeve and a spring member is provided within the protective sleeve for urging the seal member liquid-tightly against the end portion on the lead wire draw-out side of the protective sleeve. The "liquid-tightly" term referred to herein is meant to mean preventing the ingress of liquid from the exterior to the interior of the protective sleeve.

According to the present invention, since the seal member disposed in an end portion of the protective sleeve is formed of a heat-resistant synthetic resin, it is possible to improve the durability even in the case of detecting a gas component of a high temperature such as one contained in the exhaust gases of an internal combustion engine or the like. Moreover, since the seal member is urged against the end portion of the protective sleeve by the spring member, it is possible to eliminate the gap between the protective sleeve and the seal member and maintain the liquid ingress preventing property.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

The present invention will be described in detail hereinunder with reference to the drawings which illustrate several embodiments of the invention on a larger scale.

Figure 2:
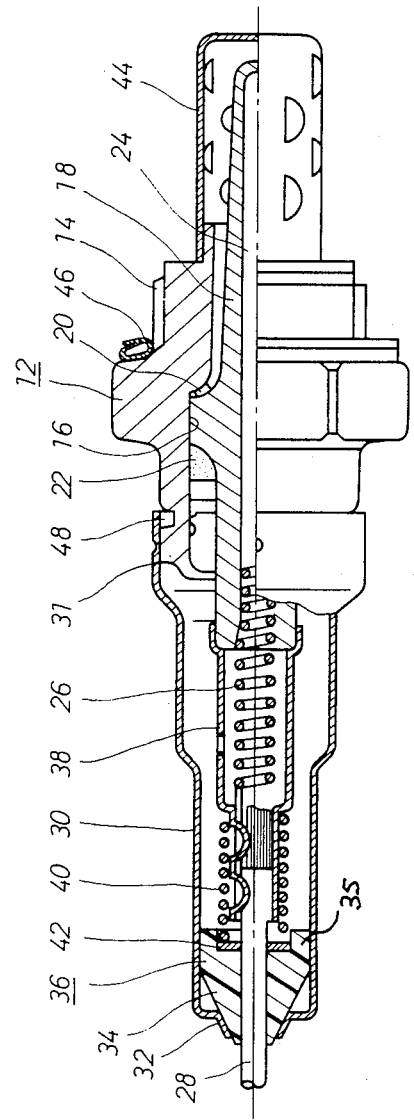
FIG. 2 is a partially sectional view of a gas sensor according to a first embodiment of the present invention.

Referring to FIG. 2, there is illustrated a gas sensor according to a first embodiment of the present invention, in which the numeral 12 denotes a metallic body. The metallic body 12 has a male screw portion 14 formed at one end portion thereof for attaching the gas sensor to the muffler of an automobile engine and a stepped through hole 16 formed centrally therein in which is inserted a zirconia element 18 for detecting oxygen and further inserted are a wire packing 20 and a talc element 22. The zirconia element 18 is centrally formed with an air chamber 24 capable of introducing and accommodating air (oxygen), and on both the outer and inner surfaces of the zirconia element 18 are formed thin platinum electrodes by plating. The outside electrode is connected to ground through the wire packing 20 and metallic body 12, while the inside electrode is electrically connected to a lead wire 28 through a spiral conductor 26 which is fitted in an inlet portion of the air chamber 24. As the spiral conductor 26 there is used a stainless steel spring material such as, for example, SUS 631 J1. The numeral 38 denotes a tubular metallic holder fitted on an open end portion of the zirconia element. The holder 38 encloses therein the spiral conductor 26 and its fore end side is attenuated to form a solderless terminal portion in which end portions of the lead wire 28 and spiral conductor 26 are connected by pressure bonding and a tensile force is imparted to the spiral conductor at all times.

On the other hand, a protective sleeve 30 is bonded to the other end portion of the metallic body 12 by spot welding. The introduction of air into the air chamber 24 is effected through a slight gap 31 formed between the inner peripheral surface of the protective sleeve 30 and the outer peripheral surface of the fitting portion of the metallic body 12. The protective sleeve 30 is attenuated stepwise toward its fore end portion, in which fore end portion is formed a tapered hole 32 so that the lead wire 28 can be drawn out through an open end of the tapered hole. Moreover, inside the fore end portion of the protective sleeve 30 is disposed a seal member 36 having a first tapered projection and a second non-tapered portion formed of polytetrafluoroethylene (trade name: Teflon), the seal member 36 being provided internally with a lead wire insertion hole and externally with the tapered projection 34. Further, between the holder 38 fitted on the zirconia element 18 and the seal member 36 is disposed a compression coil spring 40 whereby the seal member 36 is urged toward the projecting end portion of the protective sleeve 30. The urging force is practically in the range of about 1 to 3 kg. The spring urging side of the seal member 36 is in the form of a shaft in which is formed a circular recess which permits the spring 40 to be fitted therein, with a washer 42 being fitted on the bottom of the recess. The holder 38 is formed with a small hole so that the air (oxygen) which has entered from the gap 31 between the protective sleeve 30 and the metallic body 12 can be introduced through the small hole into the zirconia element 18. The numeral 44 denotes a protector for a projecting portion or the zirconia element 18, and the numeral 46 denotes a gasket.

In the oxygen sensor constructed as above, since the seal member 36 has a heat resistance characteristic it is possible to improve the durability and prolong the life in comparison with a rubber seal member. Moreover, being pressed by the spring 40, the seal member 36 is forced into and closely contacts with the tapered hole of the protective sleeve, and at the same time its lead wire insertion hole is reduced in diameter and securely holds the lead wire 28. Consequently, liquid such as water or oil can be assuredly prevented from entering the interior of the sensor from the projecting end side of the protective sleeve 30. Since the gas sensor of this embodiment is used in an upright state so that the lead wire 28 side faces almost upward, liquid such as water or oil which has adhered to the surface of the protective sleeve 30 is drained at the end portion on the metallic body 12 side of the sleeve in combination with an annular groove 48 formed in the metallic body 12 near the end portion, and is thereby prevented from entering the sensor interior.

Figure 3:
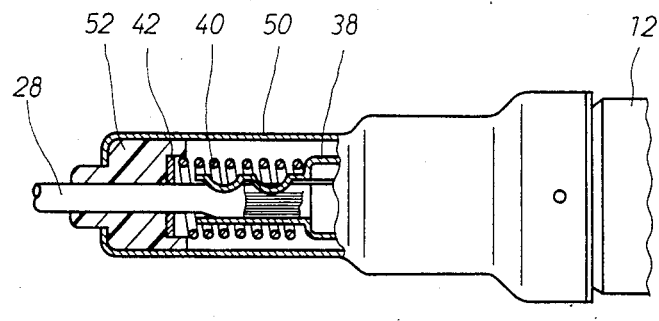
FIG. 3 is a sectional view of a principal portion of a gas sensor according to a second embodiment of the present invention.

Referring now to FIG. 3, there is illustrated a gas sensor according to a second embodiment of the present invention, in which the fore end portion of a protective sleeve 50 is drawn perpendicularly and centrally formed with a circular hole. In this circular hole is fitted a projecting portion of a seal member 52, and the lead wire 28 is inserted through an insertion hole formed in the interior of the seal member 52. The material of the seal member 52 is the same in the previous embodiment. The same portions as in the previous embodiment are indicated by the same reference numerals and their explanation is here omitted.

Figure 4:
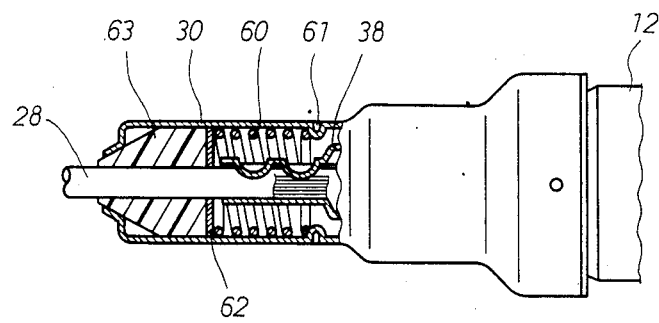
FIG. 4 is a sectional view of a principal portion of a gas sensor according to a third embodiment of the present invention.

Referring now to Fig.4, there is illustrated a gas sensor according to a third embodiment of the present invention, in which plurality of lugs 61 (four lugs in this embodiment) for fixing a compression coil spring 60 project toward the interior of the protective sleeve 30 used in the foregoing first embodiment, and a seal member 63 is biased via a washer 62 by the spring 60 one end of which is fixed by the lugs 61. In this embodiment, as is apparent from the figure, the outside diameter of the spring 60 and that of the washer 62 are about the same as the inside diameter of the protective sleeve 30, so that unlike the seal member 36, it is not necessary to form a washer fitting circular recess in seal member 63. Further, in the foregoing first and second embodiments it is necessary to perform the welding operation while pressing the metallic body 12 and the protective sleeve 30 against the spring 40 because it is not until completion of the spot welding between the metallic body 12 and the protective sleeve 30 that the spring 40 is fixed between the holder 38 and the washer 42, but in this third embodiment the welding operation can be performed more easily because the spring 60 is already fixed by the lugs 61 and the protective sleeve 30, spring 60, washer 62 and seal member 63 are integrated in advance of the welding operation.

Table 1 below shows experimental results obtained using the sensors of the above embodiments in comparison with those obtained using the prior art sensor in which only the material of the seal member has been changed. In these experiments, the sensors were heated at 300° C. for 10 hours and then allowed to stand in a room at normal temperature for 10 hours, and after repeating this ten times, air pressure of 0.2 kg/cm² was applied from the larger diameter side of the protective sleeve to the interior thereof, and the amount of air leaking from the surroundings of the seal member was measured and at the same time the appearance was visually inspected.

TABLE 1

Figure 1:
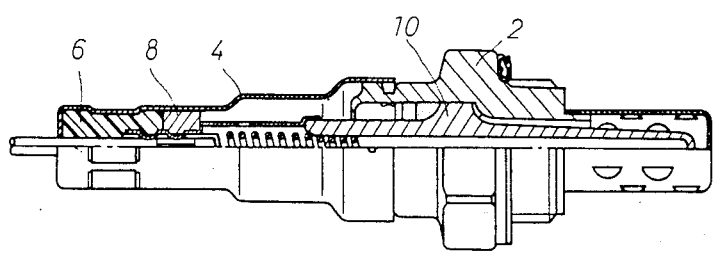
FIG. 1 is a partially sectional view of a conventional oxygen sensor.

| (Experimental results) | Air Leak | Appearance |
|---|---|---|
| 1 First Embodiment | leaks little | Good |
| 2 Second and Third Embodiments | " | " |
| 3 Prior Art | " | Seal member (6 in FIG. 1) cracked. |
| 4 Prior Art with Seal Member made of Teflon (trade name) | more than 1000 cm/min | Seal member (Teflon) was shaky. |

In the foregoing embodiments, the compression coil springs 40 and 60 may be substituted by one or more disc springs or corrugated washers as spring members. Moreover, the present invention is applicable also to other internal combustion engines than automobile engines or various combustion apparatus and further applicable to the cases where other gas components than oxygen are to be detected.

Several embodiments of the present invention have been described above, but it goes without saying that the invention is not limited thereto and various modifications may be made within the range not departing from the gist of the invention.

According to the present invention, as set forth hereinabove, since the seal member disposed in an end portion of a protective sleeve is formed of a heat-resistant synthetic resin, the durability can be improved even in the application to high temperature gases. Further, since the seal member is held in an urged state by means of a spring member, sealing is ensured and the ingress of liquid such as water or oil into the sensor interior can be prevented.

Obviously, numerous modifications and variations of the present invention are possible in light of the above teachings. It is therefore to be understood that within the scope of the appended claims, the invention may be practiced otherwise than as specifically described herein.

What is claimed is:

1. A gas sensor capable of being attached to other members, comprising:
   (a) a gas detecting element inserted into a central part of a gas sensor body;
   (b) a closed protective sleeve having a tapered hole portion at one end thereof, and attached to an end portion of said gas sensor body and having an inner circumferential surface;
   (c) a lead wire connected to said gas detecting element;
   (d) a seal member having a tapered projection engaging said tapered hole portion of said protective sleeve and a second non-tapered portion, said seal member being formed of a heat-resistant synthetic resin, the seal member being positioned within an end portion of the protective sleeve and the lead wire being positioned in and extending through the seal member wherein said non-tapered portion engages said inner circumferential surface of said protective sleeve; and
   (e) a spring member mounted within the protective sleeve, the spring member urging the seal member against an inner surface and said tapered hole portion of the protective sleeve in a liquid-tight manner said spring member also compressing said seal member into sealing contact with said lead wire so as to prevent ingress of liquid into the interior of the protective sleeve.

2. A gas sensor as set forth in claim 1 wherein said spring member further comprises a plurality of coned disc springs.

3. A gas sensor as set forth in claim 1, wherein said spring member further comprises a plurality of corrugated washers.

4. A gas sensor as set forth in claim 1, wherein said gas detecting element is a zirconia element for detecting oxygen, and said seal member formed of a heat-resistant synthetic resin is a polytetrafluoroethylene seal member.

5. A gas sensor as set forth in claim 4, wherein said one end of the protective sleeve is formed with a circular hole in a central part thereof, and the seal member is positioned in said circular hole, and wherein the lead wire is inserted through an insertion hole formed in the interior of the seal member.

6. A gas sensor as set forth in claim 1, wherein said protective sleeve is attenuated stepwise toward said one end and has a tapered portion at said one end which defines said tapered hole portion through which said lead wire extends; said seal member is provided internally with a lead wire insertion hole; and wherein said spring member further comprises a compression coil spring which urges said seal member toward the tapered portion of said protective sleeve, and further comprising:
   a plurality of lugs extending inwardly from said protective sleeve for securing said compression coil spring in position; and
   a washer disposed between said compression spring and said seal member so that the seal member can be urged through said washer by the compression spring, one end of which is fixed by said lugs, wherein an inside diameter of said protective sleeve and an outside diameter of said compression spring and that of said washer are almost equal.

7. A gas sensor as set forth in claim 6, wherein said spring member is disposed between a holder fitted on said gas detecting element and said seal member, and said gas sensor further comprising:
   a first and second platinum electrode respectively formed on the inner and outer surfaces of said gas detecting element;
   a spiral conductor connected, at one end thereof, to said electrodes formed on the inner surface of the gas detecting element and, at the other end to the lead wire, said spiral conductor being positioned in an inlet portion of an air chamber formed in the gas detecting element; a tubular holder fitted on an open-side end portion of the gas detecting element and enclosing said spiral conductor therein, an end portion of said tubular holder being attenuated to connect end portions of the lead wire and the conductor by pressure bonding.

8. A gas sensor as set forth in claim 1, wherein said protective sleeve is attenuated stepwise toward said one end and has a tapered portion at said one end which defines said tapered hole portion through which said lead wire extends; said seal member is provided internally with a lead wire insertion hole and said tapered projection of said protective sleeve is fitted to said tapered portion of said seal member; and said spring member is disposed between a tubular holder fitted on said gas detecting element and said seal member wherein said spring member further comprises a compression coil spring which urges said seal member toward the tapered portion of said protective sleeve.

9. A gas sensor as set forth in claim 8, further including:
   a first and second platinum electrode respectively formed on inner and outer surfaces of said gas detecting element;
   a spiral conductor connected, at a first end thereof, to said first electrode formed on the inner surface of the gas detecting element and, at a second end thereof, to the lead wire, said spiral conductor being positioned in an inlet portion of an air chamber formed in the gas detecting element wherein said tubular holder is positioned on an open-side end portion of the gas detecting element and encloses said spiral conductor therein, an end portion of said tubular holder being attenuated to connect end portions of the lead wire and the conductor by pressure bonding.

10. A gas sensor as set forth in claim 9, wherein a spring urging-side end portion of the seal member is in the form of a shaft and which includes:
   a circular recess formed therein to permit said compression coil spring to be fitted therein, and
   a washer fitted in said recess for engagement with said coil spring.

* * * * *